United States Patent
Fessler et al.

(10) Patent No.: US 10,856,996 B2
(45) Date of Patent: Dec. 8, 2020

(54) DISC REPLACEMENT DEVICE AND METHOD OF USE

(71) Applicant: IN QUEUE INNOVATIONS, LLC, Winona Lake, IN (US)

(72) Inventors: Richard G. Fessler, Winnetka, IL (US); John W. Boger, Saratoga Springs, NY (US); Frank S. Bono, Castle Rock, CO (US)

(73) Assignee: IN QUEUE INNOVATIONS, LLC, Winona Lake, IN (US)

( * ) Notice: Subject to any disclaimer, the term of this patent is extended or adjusted under 35 U.S.C. 154(b) by 297 days.

(21) Appl. No.: 15/817,885

(22) Filed: Nov. 20, 2017

(65) Prior Publication Data

US 2018/0140430 A1 May 24, 2018

Related U.S. Application Data

(63) Continuation of application No. 14/342,226, filed as application No. PCT/US2012/053423 on Aug. 31, 2012, now Pat. No. 9,820,864.
(Continued)

(51) Int. Cl.
*A61F 2/44* (2006.01)
*A61B 17/80* (2006.01)
(Continued)

(52) U.S. Cl.
CPC .......... *A61F 2/442* (2013.01); *A61B 17/8042* (2013.01); *A61F 2/446* (2013.01);
(Continued)

(58) Field of Classification Search
CPC ..................................... A61F 2/44–2002/4495
See application file for complete search history.

(56) References Cited

U.S. PATENT DOCUMENTS

| | | | | |
|---|---|---|---|---|
| 4,794,918 A | * | 1/1989 | Wolter | A61B 17/8042 606/295 |
| 5,258,031 A | * | 11/1993 | Salib | A61F 2/4425 623/17.15 |

(Continued)

FOREIGN PATENT DOCUMENTS

| | | | |
|---|---|---|---|
| WO | 9921502 A1 | 5/1999 | |
| WO | WO-9921502 A1 * | 5/1999 | ......... A61B 17/1655 |

OTHER PUBLICATIONS

International Search Report for PCT/US2012/053423 dated Feb. 26, 2013.
(Continued)

*Primary Examiner* — Zade Coley
(74) *Attorney, Agent, or Firm* — Heslin Rothenberg Farley & Mesiti P.C.

(57) ABSTRACT

A disc replacement device including a first body member with a convex articulation surface and a second body member with a concave articulation surface is disclosed. When operably positioned, the convex articulation surface engages the concave articulation surface to provide for movement therebetween. The disc replacement device also includes a first opening in the first body member and a second opening in the second body member, wherein the openings are angled and extends from the front aspects of the body members through the external surfaces. The disc replacement device further includes at least two bone fasteners for insertion into the first and second openings to secure the disc replacement device to a first and second vertebra. An interbody motion device and fusion implant, as well as a surgical method for implantation are also disclosed.

19 Claims, 19 Drawing Sheets

Related U.S. Application Data

(60) Provisional application No. 61/530,237, filed on Sep. 1, 2011.

(51) Int. Cl.
*A61F 2/46* (2006.01)
*A61B 17/86* (2006.01)
*A61F 2/30* (2006.01)

(52) U.S. Cl.
CPC .......... *A61F 2/4425* (2013.01); *A61F 2/4611* (2013.01); *A61B 17/86* (2013.01); *A61F 2/30767* (2013.01); *A61F 2002/305* (2013.01); *A61F 2002/30064* (2013.01); *A61F 2002/3085* (2013.01); *A61F 2002/30224* (2013.01); *A61F 2002/30232* (2013.01); *A61F 2002/30331* (2013.01); *A61F 2002/30383* (2013.01); *A61F 2002/30395* (2013.01); *A61F 2002/30433* (2013.01); *A61F 2002/30492* (2013.01); *A61F 2002/30517* (2013.01); *A61F 2002/30528* (2013.01); *A61F 2002/30607* (2013.01); *A61F 2002/30616* (2013.01); *A61F 2002/30649* (2013.01); *A61F 2002/30655* (2013.01); *A61F 2002/30662* (2013.01); *A61F 2002/30769* (2013.01); *A61F 2002/30782* (2013.01); *A61F 2002/30787* (2013.01); *A61F 2002/30808* (2013.01); *A61F 2002/30822* (2013.01); *A61F 2002/30858* (2013.01); *A61F 2310/00017* (2013.01); *A61F 2310/00023* (2013.01); *A61F 2310/00179* (2013.01); *A61F 2310/00796* (2013.01)

(56) References Cited

U.S. PATENT DOCUMENTS

| | | | | |
|---|---|---|---|---|
| 5,676,701 A * | 10/1997 | Yuan | ..................... | A61F 2/4425 623/17.15 |
| 5,888,223 A * | 3/1999 | Bray, Jr. | ............... | A61F 2/4455 623/17.16 |
| 6,019,792 A * | 2/2000 | Cauthen | ............ | A61B 17/1671 623/17.14 |
| 6,120,502 A * | 9/2000 | Michelson | .......... | A61F 2/30744 606/247 |
| 6,179,874 B1 * | 1/2001 | Cauthen | ............ | A61B 17/1671 623/17.14 |
| 6,206,922 B1 * | 3/2001 | Zdeblick | ............... | A61F 2/4611 623/17.11 |
| 6,235,034 B1 * | 5/2001 | Bray | ................... | A61B 17/1655 606/246 |
| 6,558,423 B1 * | 5/2003 | Michelson | ......... | A61B 17/7059 623/17.11 |
| 6,730,127 B2 * | 5/2004 | Michelson | .............. | A61F 2/442 623/17.16 |
| 7,147,665 B1 * | 12/2006 | Bryan | .................... | A61F 2/4425 623/17.16 |
| 7,846,207 B2 * | 12/2010 | Lechmann | ............. | A61B 17/86 623/17.11 |
| 8,709,085 B2 * | 4/2014 | Lechmann | ............. | A61B 17/86 623/17.16 |
| 2002/0022843 A1 * | 2/2002 | Michelson | ........... | A61B 17/866 606/70 |
| 2003/0135213 A1 * | 7/2003 | LeHuec | ............. | A61B 17/1671 606/86 B |
| 2004/0102848 A1 * | 5/2004 | Michelson | .............. | A61F 2/446 623/17.11 |
| 2004/0153159 A1 * | 8/2004 | Cauthen | ............. | A61B 17/1671 623/17.14 |
| 2004/0220566 A1 * | 11/2004 | Bray | ................... | A61B 17/7059 606/252 |
| 2005/0027293 A1 * | 2/2005 | LeHuec | ............. | A61B 17/1671 623/17.11 |
| 2005/0060034 A1 * | 3/2005 | Berry | .................... | A61F 2/4425 623/17.11 |
| 2006/0089717 A1 * | 4/2006 | Krishna | ............. | A61B 17/7011 623/17.11 |
| 2006/0116768 A1 * | 6/2006 | Krueger | ............. | A61B 17/1757 623/17.14 |
| 2006/0122703 A1 * | 6/2006 | Aebi | ..................... | A61F 2/4425 623/17.15 |
| 2006/0259147 A1 * | 11/2006 | Krishna | ................ | A61F 2/4611 623/17.15 |
| 2008/0300685 A1 | 12/2008 | Carls et al. | | |
| 2010/0286777 A1 * | 11/2010 | Errico | ..................... | A61F 2/442 623/17.11 |

OTHER PUBLICATIONS

International Preliminary Report on Patentability for PCT/US2012/053423 dated Mar. 13, 2014.
Supplemental Partial European Search Report for European Application No. 12827605 dated Apr. 27, 2015.
European Search Report for European Application No. 12827605 dated Sep. 21, 2015.

* cited by examiner

DISC REPLACEMENT DEVICE AND METHOD OF USE

CROSS-REFERENCE TO RELATED APPLICATION

This application is a continuation of U.S. Non-Provisional patent application Ser. No. 14/342,226 filed on May 20, 2014 (U.S. Pat. No. 9,820,864) which application was a 371 Application of PCT Application No. PCT/US2012/053423 filed on Aug. 31, 2012, which claims the priority benefit under 35 U.S.C. § 119(e) of U.S. Provisional Patent Application No. 61/530,237 filed Sep. 1, 2011, each of which is incorporated herein by reference in their entireties.

TECHNICAL FIELD

The present invention relates generally to general surgery, orthopaedic and neurosurgical implants used for insertion within a space between hard tissue structures, and more specifically, but not exclusively, concerns devices implanted between vertebral bodies to replace a resected or diseased intravertebral disc to maintain or reestablish proper spacing between two vertebral bodies.

BACKGROUND OF THE INVENTION

Damage or disease that affects the integral structure of the spine, may lead to neurologic impairment or loss of structural support integrity with possible permanent damage to the surrounding soft tissue and adjacent neurologic, vascular and systemic structures. Maintaining or reestablishing anatomic spacing within the spinal column is critical to ensuring continued functionality and mobility of the patient and avoidance of long-term serious neurological, vascular or other systemic impairments.

SUMMARY OF THE INVENTION

Advancement of the state of interbody devices and implants and the surgical management relating to the clinical presentation of damaged tissue structures between two vertebral bodies is believed desirable. Two examples of embodiments of the invention that satisfies the need for improvements to an interbody disc device used to treat patients suffering from either a diseased or damaged disc includes at least one moveable top member and a stationary bottom member that is slidingly coupled to the moveable top member.

The present invention provides in one aspect, a disc replacement device that has a first body member that includes a convex articulation surface and a second body member including a concave articulation surface. When operably positioned, the convex articulation surface of the first body member engages the concave articulation surface of the second body.

In another aspect of the present invention, the disc replacement device has a generally cylindrical geometry. The first body member also includes an external inferior surface and a top internal surface and the second body member includes an external superior surface and a bottom internal surface. The external superior surface and external inferior surface are arcuate. The top internal surface of the first body member may include a flat portion with a convex portion in a generally central position on the flat portion and extending away from the flat portion to create the convex articulating surface. The bottom internal surface of the second body member including a flat portion with a concave portion in a generally central position on the flat portion and extending into the second body member from the flat portion to create the concave articulating surface.

In a further aspect of the present invention, the disc replacement device may include first and second openings in the first and second body members where the first and second openings are angled and extend from a front aspect of the first and second body members through the external surfaces. The angled openings include an angle ranging from about 10° to about 45°. The disc replacement device may further include at least two bone fasteners for insertion into the first and second openings to secure the device to a first and second vertebra.

The present invention provides in another aspect an interbody motion device that includes a bottom body member having a convex surface, a top body member having a channel, and a bearing member having a concave surface. The bearing member is connected to the channel with the concave surface of the bearing member engaging the convex surface of the bottom body member when the device is in use. The interbody motion device wherein the concave surface of the bearing member is configured to permit at least one of translation and rotation of the convex surface of the bottom member. The interbody motion device may also include an outside surface that is generally arcuate. The interbody motion device further comprising first and second openings extending from the front surfaces of the members and existing through the outside surface of the members.

The present invention provides in yet another aspect, an interbody motion device with a locking device which includes a plate and at least one leg extending perpendicular from the plate. The locking device couples the top body member, bearing member, and bottom body member together and inhibit motion therebetween. The interbody motion device may also include a relief edge on the front surfaces of the top body member, bearing member, and bottom body member and a relief edge on the rear surfaces of the top and bottom body members.

The present invention provides in yet another aspect, a fusion implant that has a first body member having a domed articulation surface and a second body member having a dished articulation surface. The fusion implant also has a means to restrict motion when the means is operably positioned intermediate adjacent to the domed articulation surface of the first body member and the dished articulation surface of the second body member. The means to restrict motion in the fusion implant includes a plate member for insertion into a front end of the implant and at least one fastening mechanism for securing the plate member to the first and second body members.

In yet another aspect, the present invention provides a disc replacement device including a first body member, a second body member, a front end and back end, wherein a longitudinal axis extends from the front end to the back end. The first body member including a flat interior surface, an arcuate exterior surface adjoining the lateral sides of the flat interior surface, and a concave portion extending into the first body member form the flat interior surface. The second body member including a flat interior surface, an arcuate exterior surface adjoining the lateral sides of the flat interior surface, and a convex portion extending away from the flat interior surface of the second body member. The concave and convex portions are positioned generally centrally along the longitudinal axis. When operably positioned, the convex portion of the second body member engages the concave portion of the first body member to provide for movement therebetween.

The present invention provides in another aspect, a surgical method for maintaining a space between two vertebral bodies in a spine of a patient that includes the steps of obtaining a medical device that has a first body member with a convex articulation surface and a second body member having a concave articulation surface. When the first body member and the second body member are operably positioned, the convex articulation surface of the first body member engages the concave articulation surface of the second body. The method may also include the step of inserting and coupling a holding tool into an opening within the medical device. The method may further include the step of rotatably inserting the medical device into a space between two vertebral bodies. The method may further include the step of disengaging the holding tool to remove the tool from an opening in the patient.

The surgical method may further include drilling holes through the first and second openings in the first and second body members into a first and second vertebra and inserting first and second bone fixation devices through the first and second openings.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

DETAILED DESCRIPTION FOR CARRYING OUT THE INVENTION

Generally stated, disclosed herein is a disc replacement device or interbody dynamic disc implant that typically includes a top member, a bottom member and a removable bearing insert. An alternative embodiment of the disc replacement device may include a top member with an integral bearing component and a bottom member with an integral articulating component. As used herein, the terms "disc replacement device", "device", "interbody disc implant," "interbody motion device," and "implant" may be used interchangeable as they essentially describe the same type of device. Further, a corresponding insertion tool used for the implantation of the disc replacement device is discussed. Finally, described herein is a surgical method (both open and minimally invasive) for using the disc replacement device to maintain a space between two vertebral bodies within a patient suffering from a diseased or damaged disc within the spinal column.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant nearest the torso, while "distal" indicates the portion of the implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

Figure 1:
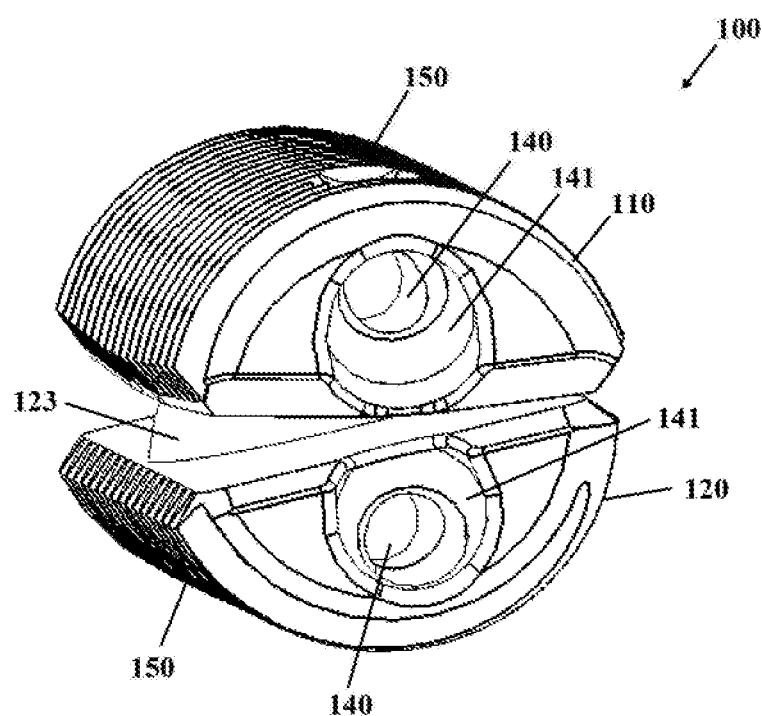
FIG. 1 is a perspective view of one embodiment of a disc replacement device, in accordance with an aspect of the present invention.
Figure 2:
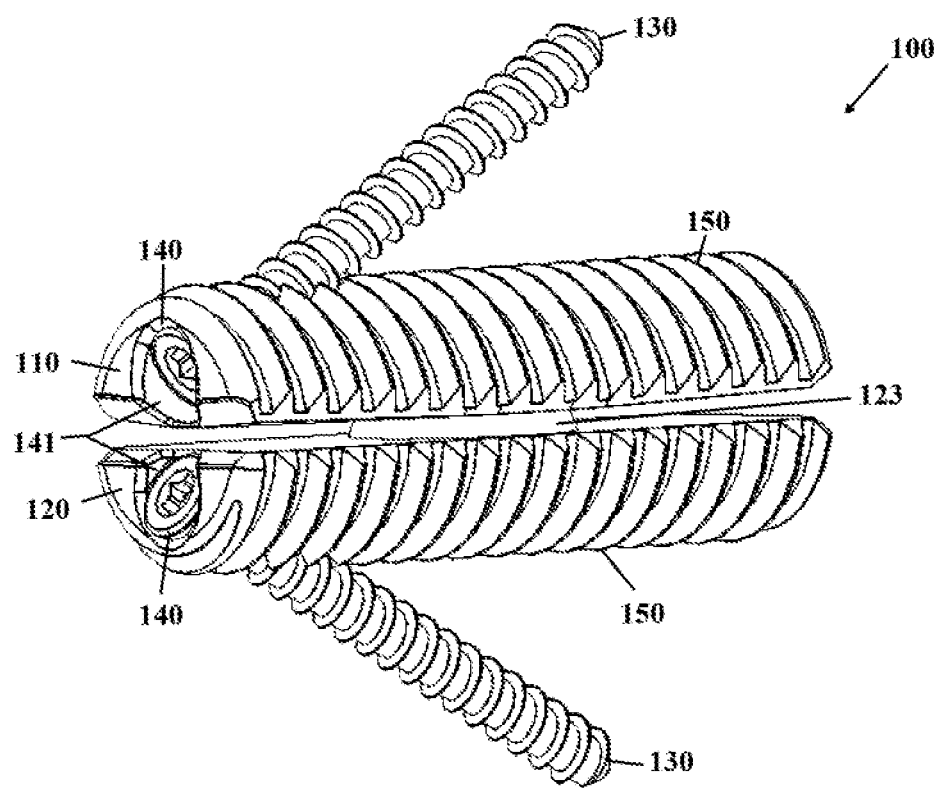
FIG. 2 is a perspective view of the disc replacement device of FIG. 1 with two inserted bone fixation devices, in accordance with an aspect of the present invention.
Figure 3:
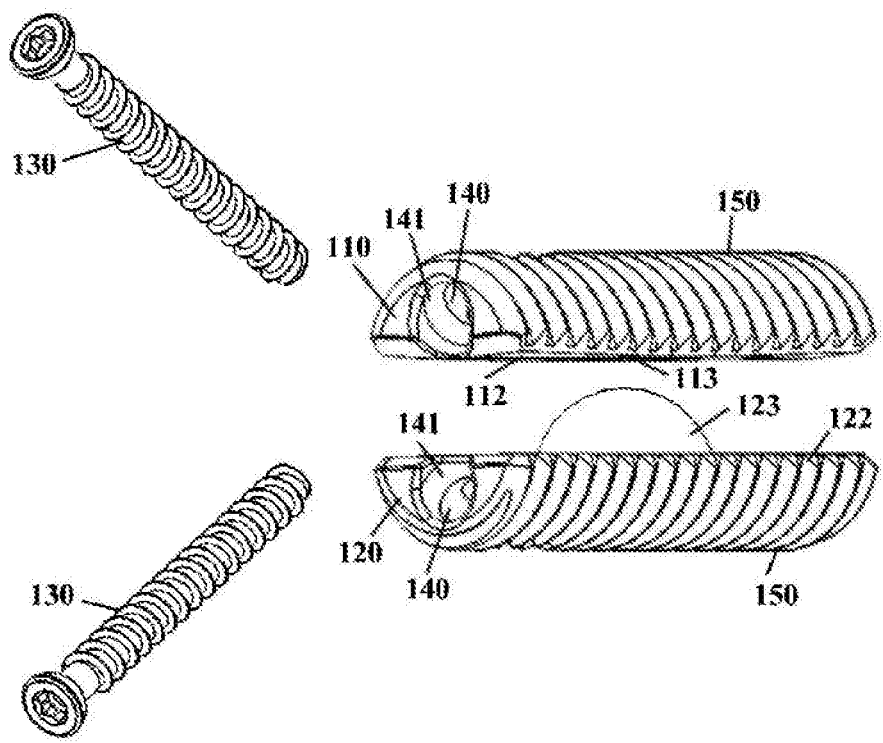
FIG. 3 is an exploded view of the disc replacement device of FIG. 1, in accordance with an aspect of the present invention.

It is shown in FIG. 1, the example of the disc replacement device 100. The device 100 as seen in FIGS. 1, 2, 3, 4 and 5 has a generally cylindrical geometry with an either straight or tapered external profile to facilitate insertion between two vertebral bodies. The implant 100 may likely include a top member or second body member 110 and a bottom member or a first body member 120. As seen in FIG. 2, for example purposes, two bone fixation devices or bone fasteners 130 are inserted through the front aspect of the top member 110 and bottom member 120 to enhance stability of the device following insertion between the vertebral bodies. The top and bottom members 110, 120 may also include rear aspects parallel to the front aspects. The bone fixation devices 130 as seen in FIGS. 2 and 3 are cancellous bone screws although other fixation devices may be employed, including but not limited to posts, deployable fins, alternative threaded screws, nails, pegs and pins. Various surface coatings may be applied to these fixation devices to enhance securement to the bone.

As depicted in FIGS. 2 and 3, the bone fixation devices are inserted through two respective holes 140 that extend at an angle from the front face of the top member 110 and the bottom member 120 through the external superior surface 150 and the external inferior surface 150 of the respective top member 110 and bottom member 120, respectively. The external superior surface 150 and external inferior surface 150 may have a generally arcuate shape. For example purposes, the trajectory of the holes may be within a range of between 10 and 45 degrees with a preferred angulation of 30 degrees. It is contemplated that the holes may be configured to allow for variable angulation of the screws to facilitate bone purchase when insertion occurs. The diameter of the holes may be between 2.5 and 5.5 mm with a preferred diameter of 3.5 mm. The entry port 141 for the hole may allow for rotation or pivoting of the corresponding bone fixation device head or alternatively, the hole opening may provide for a mechanism to lock the bone fixation device head in a set position.

Figure 4:
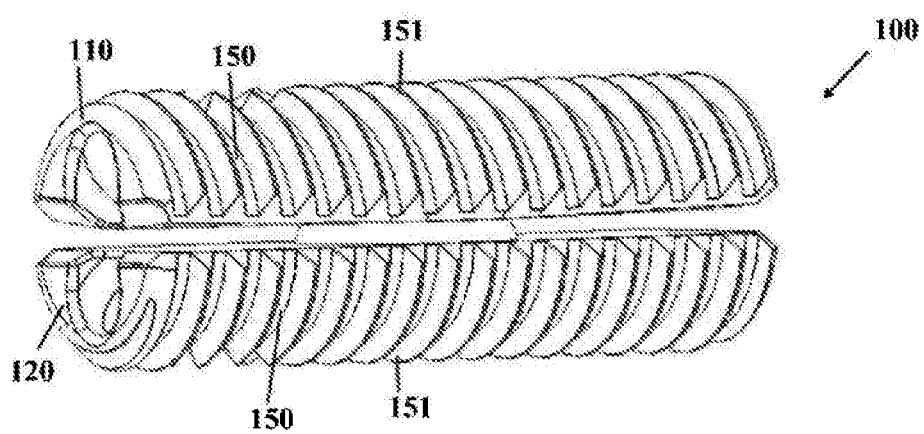
FIG. 4 is a perspective view of the disc replacement device of FIG. 1 prior to the insertion of two bone fixation devices, in accordance with an aspect of the present invention.
Figure 5:
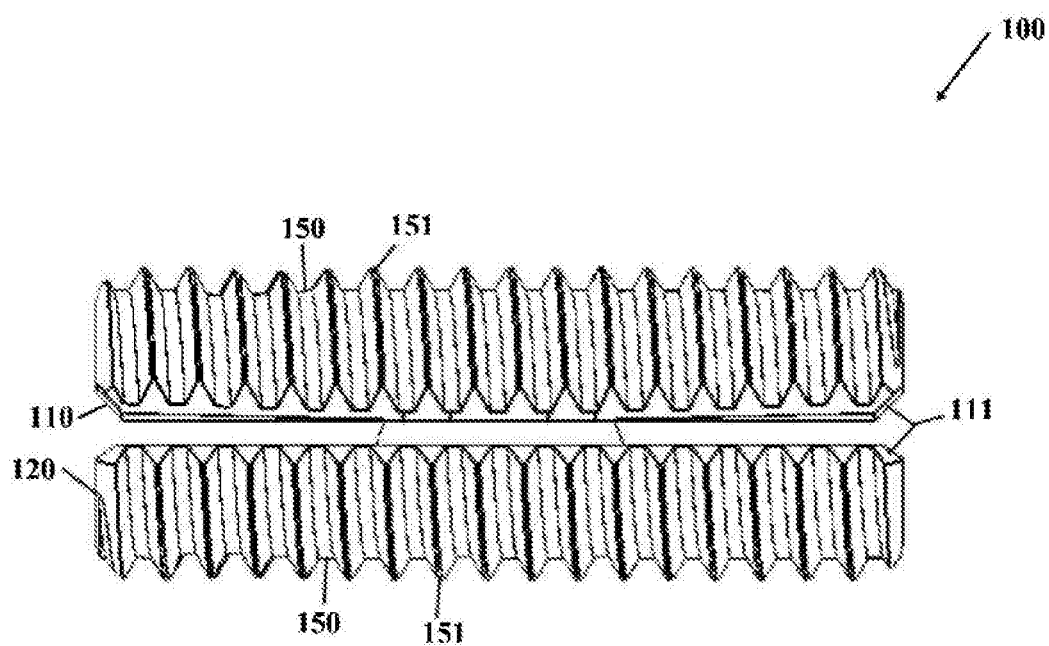
FIG. 5 is a side view of the disc replacement device of FIG. 1 prior to the insertion of two bone fixation devices, in accordance with an aspect of the present invention.

FIGS. 4 and 5 show the top member 110 and the bottom member 120 operatively positioned relative to each other. The resulting longitudinal profile of the device cylindrical structure may be straight or incorporate a slight taper. The overall length of the cylinder may range from 35 to 55 mm with a preferred length of approximately 44 mm. As seen in FIG. 5, a chamfer, relief, relief edge, radius, or other like material break 111 is present to facilitate movement between the top and bottom members.

The device 100 as shown has a diameter of approximately 17 mm, although it is understood that the device may be offered with a wide range of diameters to accommodate the various clinical situations that are presented. The range of diameters may be between 12 and 25 mm with a preference cross-section of approximately 17 mm.

Figure 8:
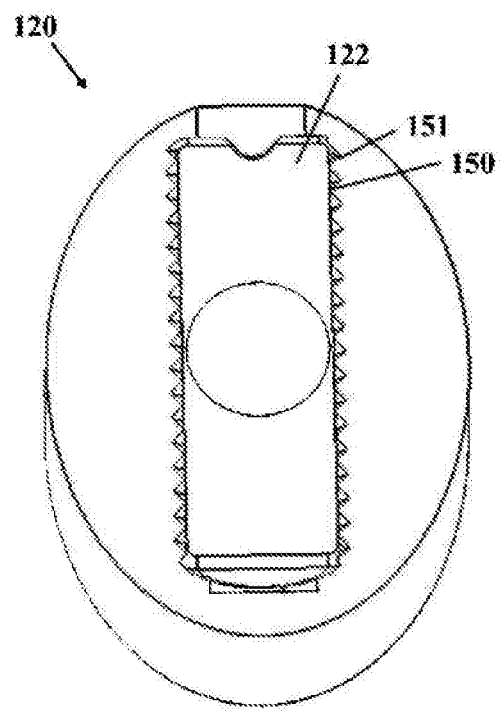
FIG. 8 is a superior, posterior view of the bottom member of the disc replacement device of FIG. 1, implanted within a vertebral body, in accordance with an aspect of the present invention.
Figure 12:
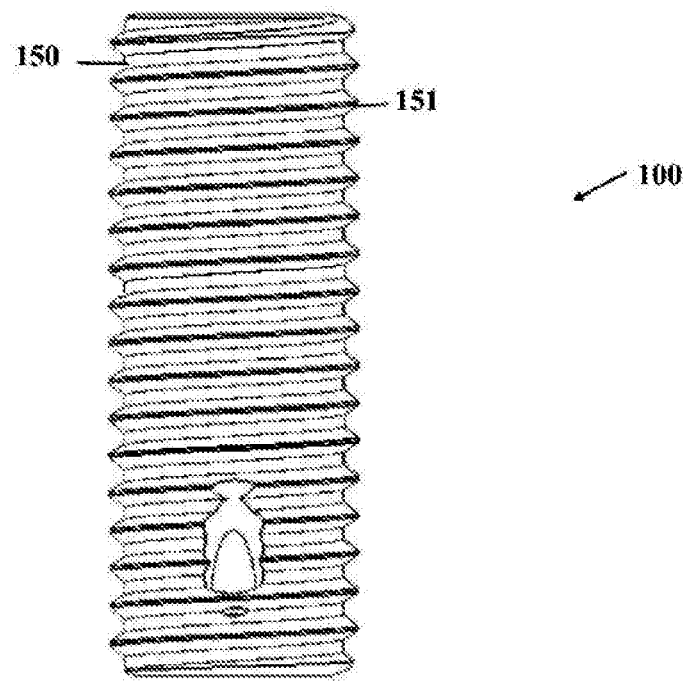
FIG. 12 is an superior view of the superior threaded surface of the top member of the disc replacement device of FIG. 1, in accordance with an aspect of the present invention.

FIGS. 4, 5, and 12 show the external surfaces 150 for both the top member 110 and the bottom member 120 to be threaded. The threads 151 run continuously for the entire circumference and length of the device. For example purposes, as shown in these figures, the thread configuration is a buttress thread with a thread depth of 1 mm, the thread type and depth may be altered depending upon the quality of bone into which the device 100 is being threaded. As seen in FIG. 8, the thread configuration will allow for variable depth of penetration into the vertebral endplate. For example purposes, as shown in FIG. 8, the depth of penetration into the bone is approximately 3 mm. It is also contemplated that the external surface 150 and corresponding threads 151 may be coated in some manner with a bone growth substance, including but not limited to TCP, HA, MP or other similar material. It is further contemplated that the external surfaces 150 may be non-threaded and that such surfaces may be configured with alternative surface engaging structures, including but not limited to, ribs, spikes, scallops, and porous coating.

FIG. 5 exhibits the continuity of the threads 151 between the top and bottom members when the two members are operatively positioned. Having the threads 151 run in a continuous circumferential manner allows the operating surgeon to screw the device 100 into two adjacent vertebral endplates while maintaining the alignment and orientation of the top member 110 and bottom member 120 relative to each.

Figure 6:
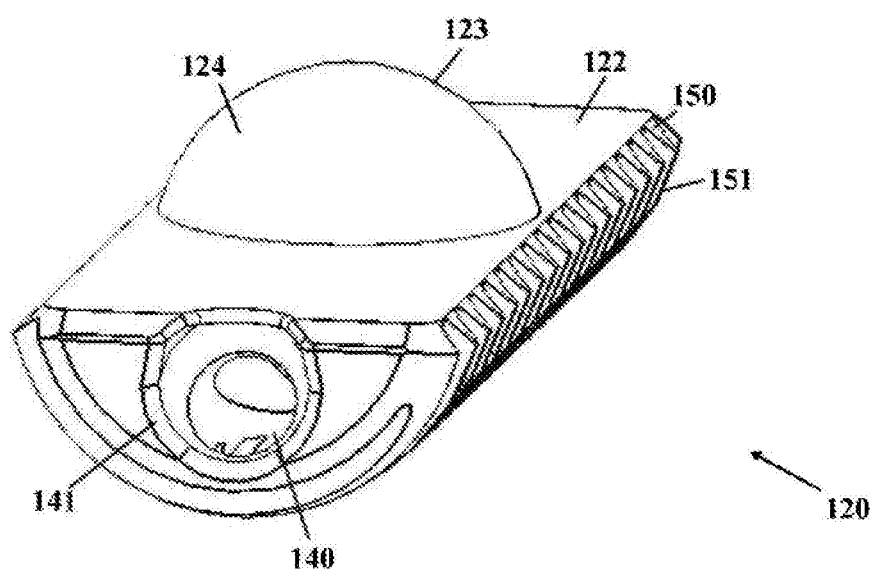
FIG. 6 is a superior, perspective view of a bottom member of the disc replacement device of FIG. 1, in accordance with an aspect of the present invention.
Figure 7:
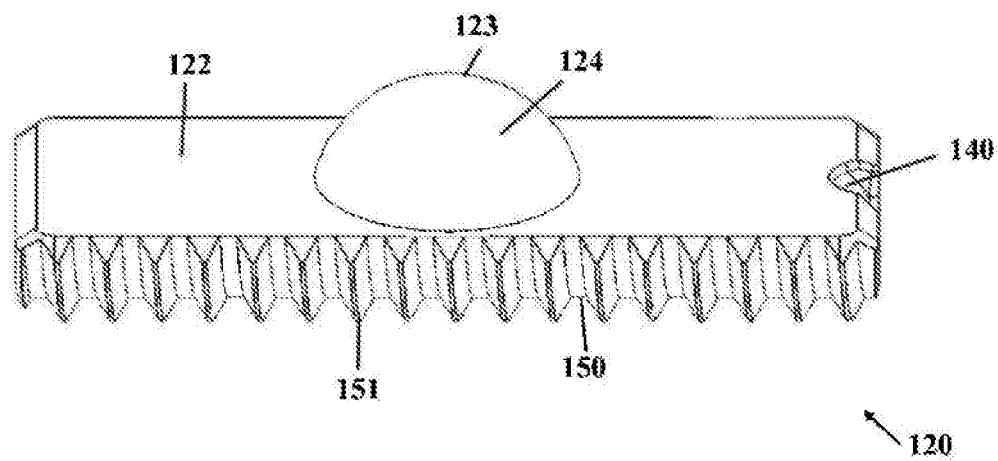
FIG. 7 is a superior, side view of the bottom member of the disc replacement device of FIG. 1, in accordance with an aspect of the present invention.

Looking at the bottom member 120 alone, FIGS. 6 and 7 show generally the configuration of this aspect of the device. The member 120 as shown is a solid body, although it may be a hollow construct. As described above, the external surface 150 is threaded. The superior aspect of the bottom member 120 is comprised of a flat surface or portion 122 that runs the entire length of the bottom member 120. Positioned in the central region of the flat surface 122 is an arcuate or ball-shaped element 123 that extends from the flat surface 122. (Other spherical shapes may also be used for the arcuate element or convex portion 123). The arcuate element 123 creates a convex articulation surface. The "ball" is typically 14 mm in diameter although the device 100 may be available with various sized balls ranging between 10 and 20 mm. As seen in FIG. 7, the arc of the ball (as measured from one side of the flat surface to the opposite side of the flat surface) as shown is slightly less than 180 degrees, although it is contemplated that device 100 be made with a varying arc of between 140 and 180 degrees with a preferred included angle of 150 degrees. The surface 124 of the ball is smooth to allow for low friction articulation with the top member 110.

Figure 9:
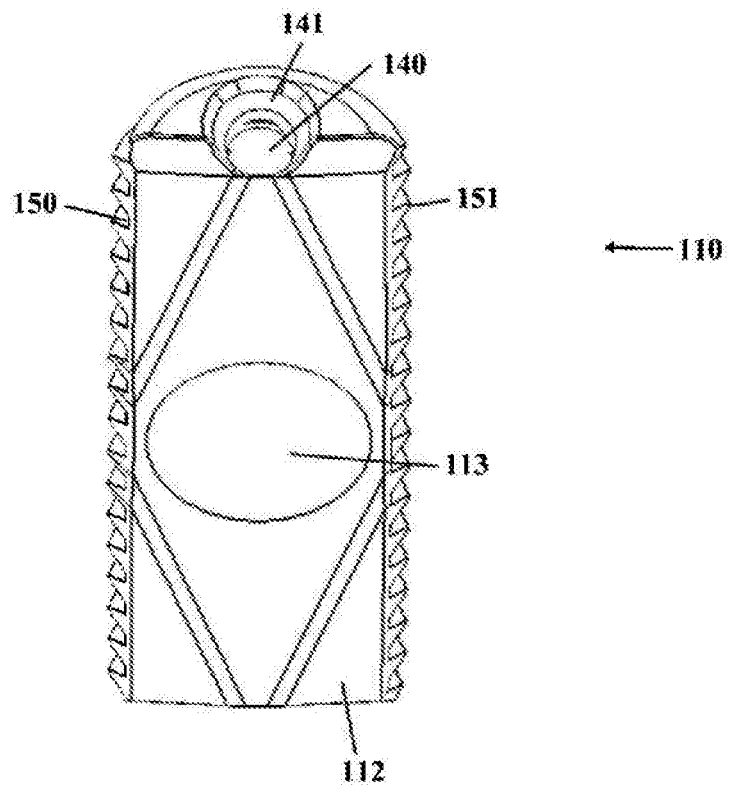
FIG. 9 is an inferior, perspective view of a top member of the disc replacement device of FIG. 1, in accordance with an aspect of the present invention.
Figure 10:
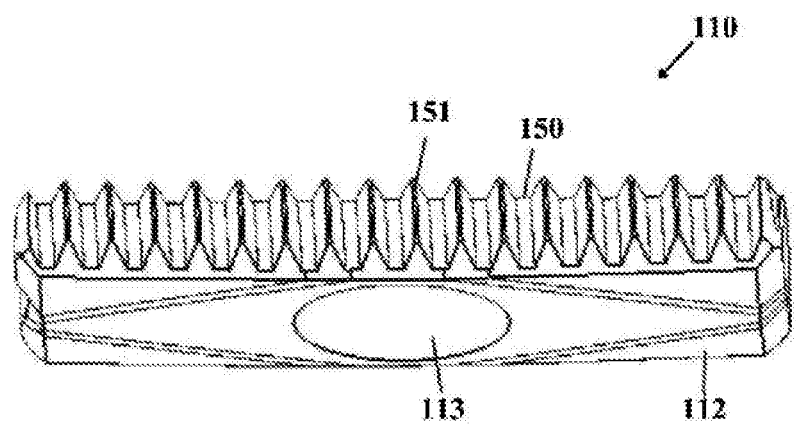
FIG. 10 is an inferior, side view of the top member of the disc replacement device of FIG. 1, in accordance with an aspect of the present invention.
Figure 11:
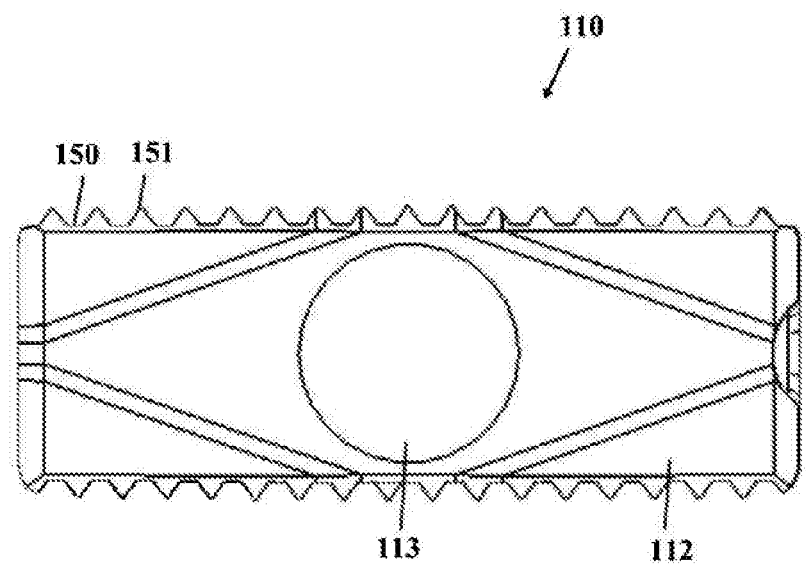
FIG. 11 is an inferior view of the top member of the disc replacement device of FIG. 1, in accordance with an aspect of the present invention.

The top member 110 is shown alone in FIGS. 9, 10 and 11. Like the bottom member 120, the top member 110 may be a generally solid construct. As shown in these figures, the inferior aspect of the top member 110 is comprised of a flat surface or portion 112 with a concavity or arcuate depression 113 located along the device midline and is centralized relative to the outer perimeter of the top member 110. The arcuate depression or concave portion 113 creates a concave articulation surface. The diameter of the depression or "socket" 113 is sized to receive the ball 123 and provide for low friction movement between the top member 110 and the bottom member 120. The socket 113 surface is prepared in a manner to ensure the socket 113 functions as a bearing surface to facilitate smooth articulation between the top member 110 and the bottom member 120.

Figure 20:
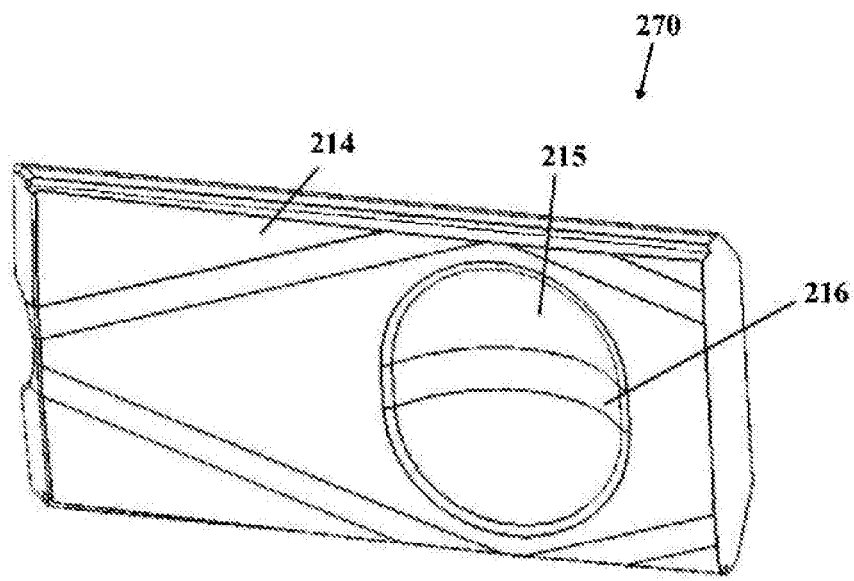
FIG. 20 is as side perspective, inferior view of an alternative embodiment of a bearing insert used in the disc replacement device of FIG. 13, in accordance with an aspect of the present invention.

Although not shown with the embodiment of the device 100 it is contemplated that the socket 113 may not be comprised of a constant radius but include a relatively flat portion at the apex resulting in a trough like depression (See FIG. 20). For example purposes, the length of the flat portion may allow the ball 123 to translate over a certain distance either in the anterior to posterior direction or alternatively, in the medial to lateral direction when the top member 110 is articulated through a full range of motion relative to the bottom member 120. The length of the flat portion in the trough depression may be varied depending upon a given clinical situation to provide the operating surgeon with the flexibility to adjust the resultant amount of translation required for a particular patient.

As seen in FIGS. 1, 2 and 3, ball 123 of bottom member 120 articulates within the socket 113 of top member 110. When operatively positioned, the device 100 will allow for a full range of between 10 and 20 degrees of anterior/posterior or flexion/extension motion. Preferably, the full range of motion will be between 13 and 15 degrees of flexion/extension. This equates to approximately 6½ to 7½ degrees of flexion and an equal amount of extension as measured from a neutral position. It should be noted that the device final range of motion may be impacted by the amount of thread contact that occurs with the bone following the insertion of the device 100 into the adjacent vertebral bodies, such as a first vertebra and a second vertebra. Additionally, the device 100 is configured to allow for a range of lateral bending of between 4 and 12 degrees, with the preferred range being between 6 and 10 degrees. This equates too approximately between 3 and 5 degrees for each side of lateral bending. The device 100 in operation may flex and extend at the same time that lateral bending motion is occurring. Finally as noted above, in the event that a trough depression is used within the top member, along with the flexion/extension and lateral bending motion, anterior to posterior translation may also be occurring. The distance of such translation will depend upon the length of the flat portion within the trough depression. It should be understood that the ranges of motion provided above are for examples purposes only and may increase or decrease depending upon several structural elements of the device 100 as well as anatomic features of the patient.

A second embodiment of disc replacement device 200 is shown in FIGS. 13-17. The device 200 as seen in the exploded views of FIGS. 16 and 17 has a generally cylindrical or arcuate geometry similar to device 100 with an either straight or tapered external profile to facilitate insertion between two vertebral bodies. The implant 200 may likely include a top body member 210, a bottom body member 220, two bone fixation devices 230 (see FIGS. 13 and 14) which are inserted through the front aspect of the top and bottom members 210, 220 to enhance stability of the device following insertion between the vertebral bodies. The top and bottom members 210, 220 may also include rear aspects parallel to the front aspects. Also seen is a third element, a modular bearing insert 270 that couples with the top member 210. As used herein, the terms "modular bearing insert," "bearing member," "bearing insert" and "replaceable bearing insert" may be used interchangeable as they each refer to the same component. Both of the devices 100, 200 have similar structural members, so for brevity sake, these same elements will not be discussed again and it should be understood that the limitations disclosed above for device 100 are the same as for device 200. These same elements include the bottom member 220 including ball 223, the bone fixation devices 230, the holes 240 and the external surface 250.

Figure 15:
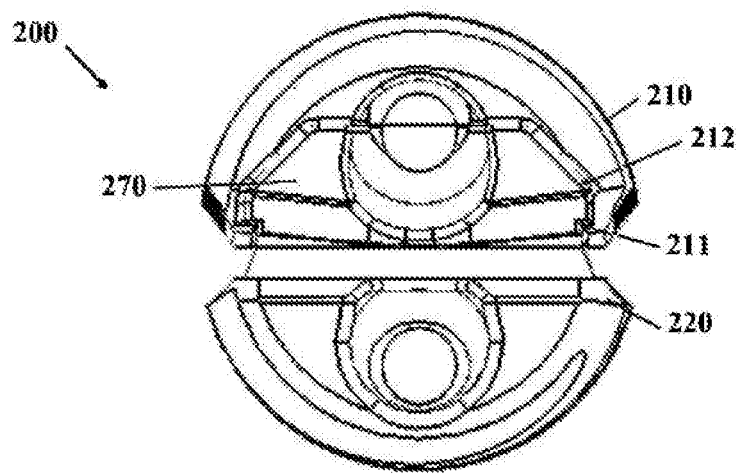
FIG. 15 is an enlarged view of the front aspect of the disc replacement device of FIG. 13, in accordance with an aspect of the present invention.
Figure 16:
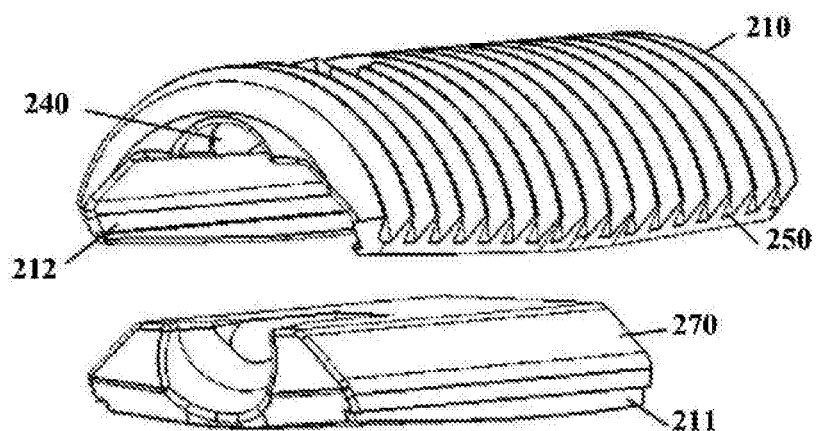
FIG. 16 is an exploded perspective view of the disc replacement device of FIG. 13, showing a top member, a bottom member and a bearing insert, in accordance with an aspect of the present invention.
Figure 16:
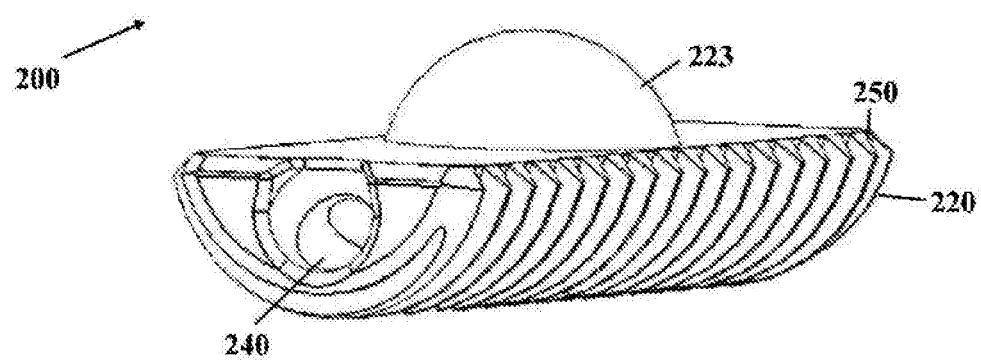
Figure 17:
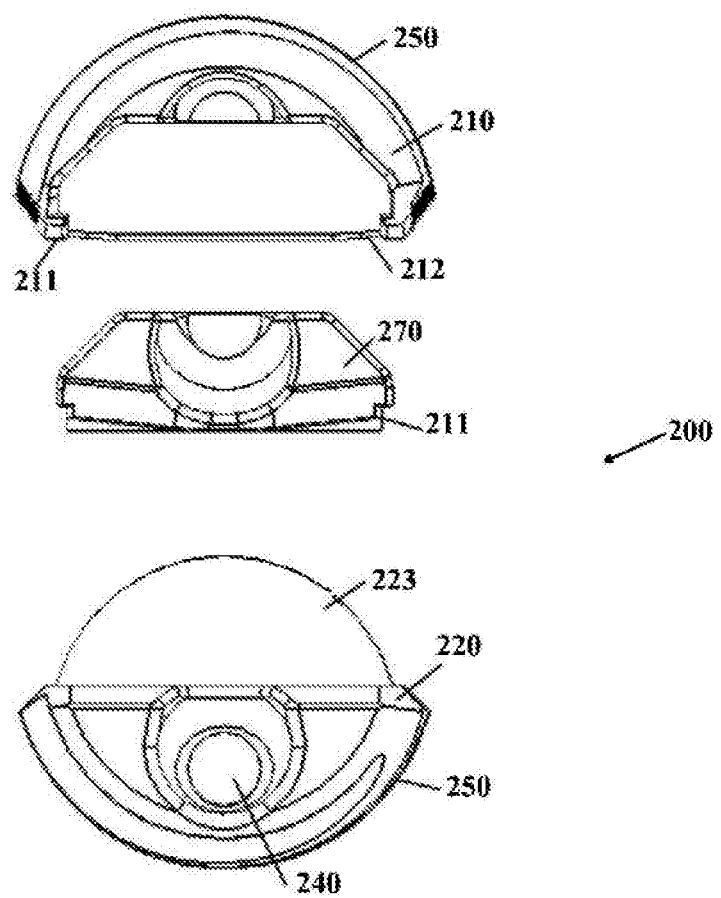
FIG. 17 is an exploded front view of the disc replacement device of FIG. 13, showing the top member, the bottom member and the bearing insert, in accordance with an aspect of the present invention.
Figure 18:
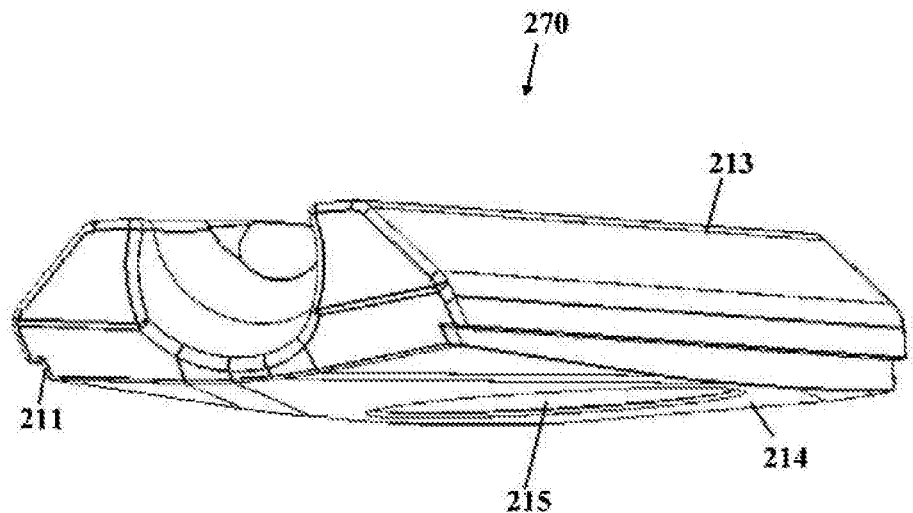
FIG. 18 is a side perspective view of the bearing insert of the disc replacement device of FIG. 13, in accordance with an aspect of the present invention.
Figure 19:
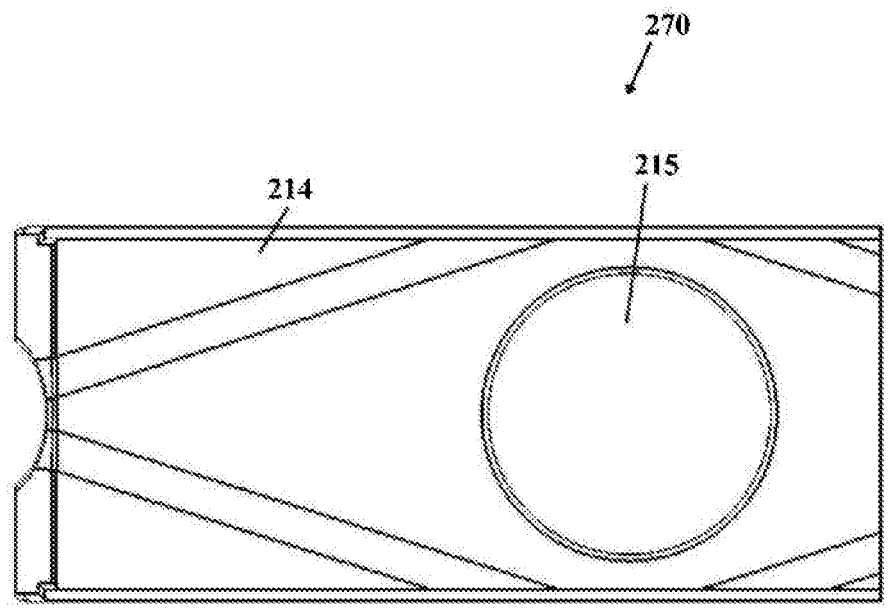
FIG. 19 is an inferior view of the bearing insert of the disc replacement device of FIG. 13, in accordance with an aspect of the present invention.

Top member 210 is modular in design in that it includes a replaceable bearing insert 270. The bearing insert 270 is slid into a channel 212 that is positioned between two retaining mechanisms, which for example is shown in FIG. 15 as a lip or dovetail arrangement 211. The bearing insert 270 as seen in FIG. 18 is generally rectangular in shape to fit within the corresponding channel 212 in the top member 210. The bearing insert 270 includes a flat top surface 213, a flat bottom surface 214 with a depression or "socket" 215. As shown in FIG. 19, the diameter of the socket 215 is sized to receive the ball 223 of the bottom member 220 and provide for low friction movement between the top member 210 and the bottom member 220. The socket 215 surface is prepared in a manner to ensure the socket 215 functions as a bearing surface to facilitate smooth articulation between the top member 210 and the bottom member 220. The modular bearing insert 270 provides the operating surgeon with flexibility to adjust the overall device thickness and ensure proper spacing between the two vertebral bodies has been achieved.

Figure 21:
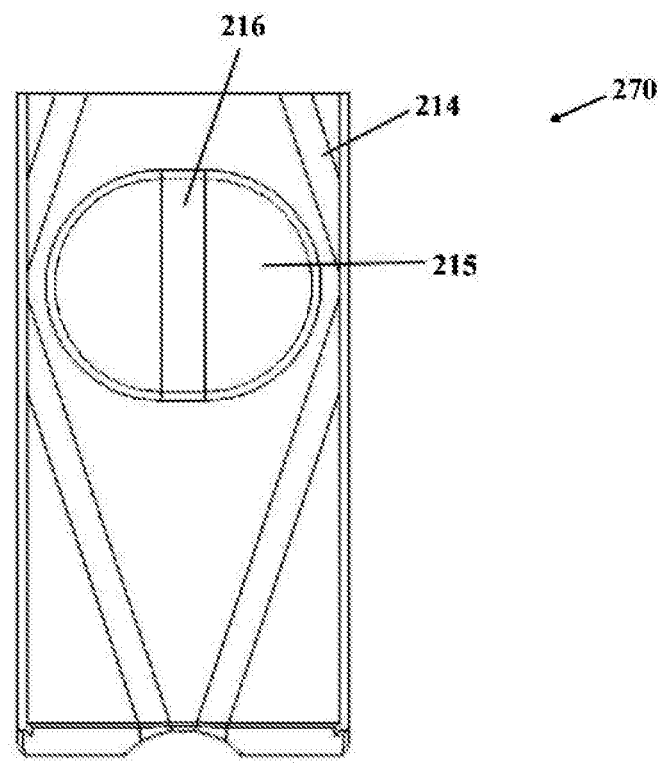
FIG. 21 is an inferior view of the alternative embodiment of the bearing insert of FIG. 20 used in the disc replacement device of FIG. 13, in accordance with an aspect of the present invention.

As seen in FIGS. 20 and 21, socket 215 may also be elongated or configured more like a trough to allow for translational movement between the bearing insert 270 and the ball 223. As described above, at the apex of the socket 215 a flat portion 216 exists that allows the ball 223 to slide rather than roll along the surface of the socket 215. From a functional perspective, this means that when assembled, top member 210 would allow bottom member 220 to translate a finite distance before rolling or pitching motion occurs following the implantation of the device between two adjacent vertebral bodies.

Figure 13:
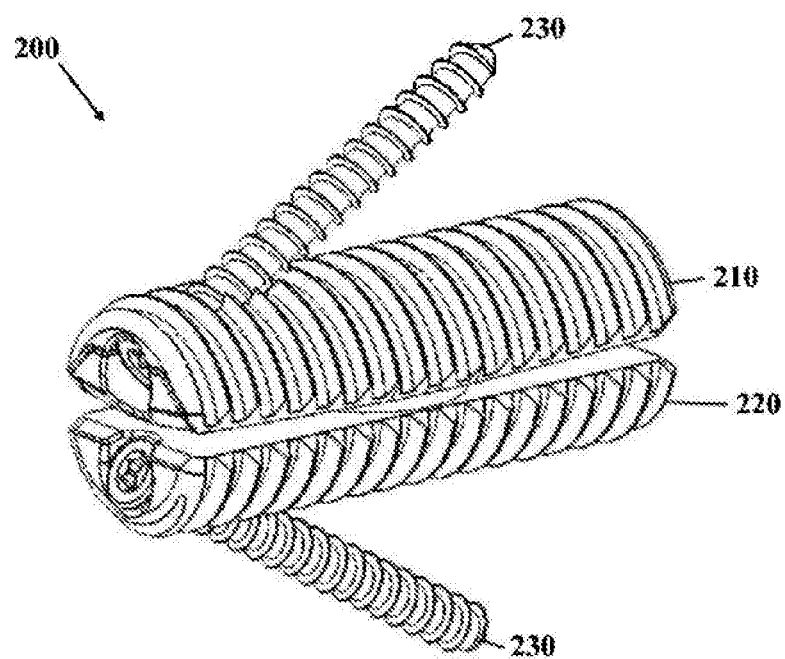
FIG. 13 is a perspective view of a second embodiment of a disc replacement device, in accordance with an aspect of the present invention.
Figure 14:
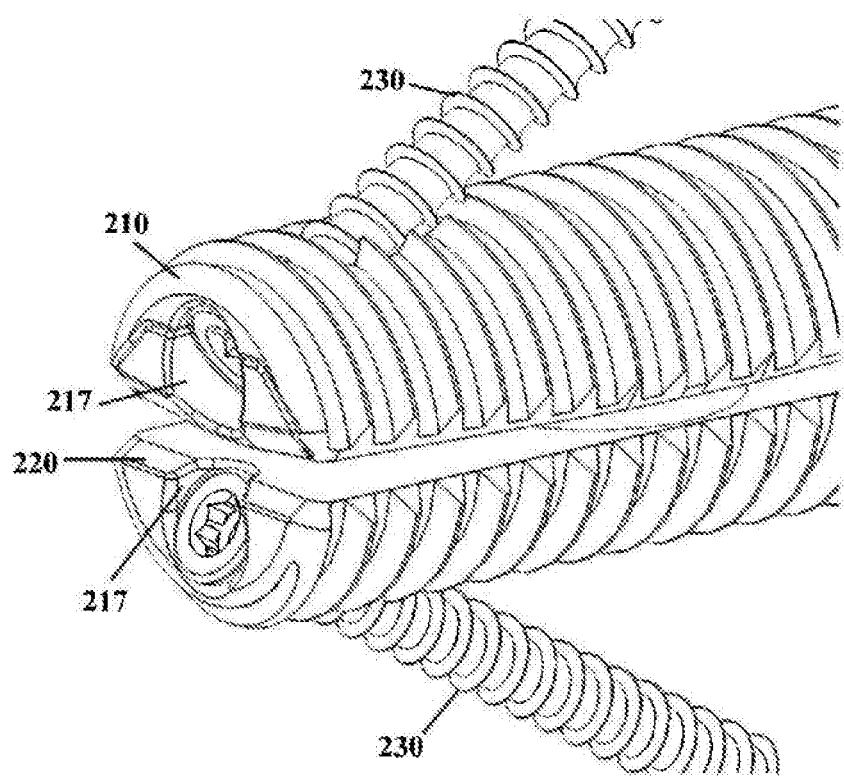
FIG. 14 is an enlarged perspective view of the front aspect of the disc replacement device of FIG. 13, in accordance with an aspect of the present invention.

The method of assembling the top member 210 may include the steps of choosing which configuration of the socket 215 the operating surgeon would like to utilize. Following the selection, the surgeon would slide the bearing insert 270 into the retention mechanisms, which as shown in FIGS. 14 and 15 are dovetails 211. The device 200 is then assembled with the top member 210 and bottom member 220 being screwed together into the adjacent vertebral bodies. Following insertion into the bones, the bone fixation devices 230 are inserted through holes 240. As seen in FIG. 13, the heads of the bone fixation devices 230 will lock the bearing insert 270 into the channel 212 of the top member 210. It is understood that other locking mechanisms or anti-kickout devices may be used, including swags, spring locks, pins, press-fit locks, etc. Please note that the holes 240 and entry ports 217 and the resultant angulation of the bone fixation devices 230 are similar to those described above for device 100.

Several biocompatible materials may be used to fabricate the elements, including the insert, of both embodiments of the disc replacement device 100, 200. These may include a myriad of metals, polymers, ceramics and composites. Examples of these include PEEK, titanium and stainless steel.

FIGS. 26-29 show an insertion instrument 500 that may be used with devices 100, 200. The instrument 500 includes a handle 501 and an alignment head 502. The head 502 may include a spacer 503 and at least one prong 504. The example instrument 500 is shown with a superior and inferior prong 504.

Figure 27:
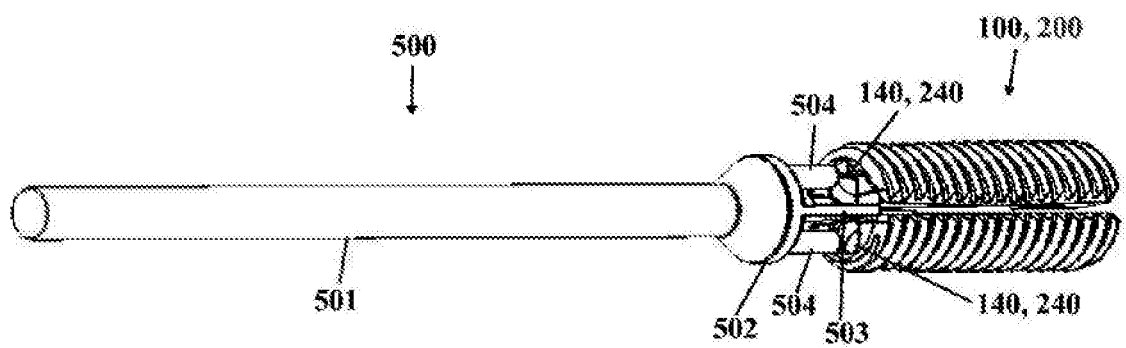
FIG. 27 is perspective elevational view of the insertion tool of FIG. 26 prior to insertion in the disc replacement device of FIG. 1, in accordance with an aspect of the present invention.

FIG. 27 shows the instrument 500 in position prior to insertion into the device 100, 200. The prongs 504 are seen to be aligned with the holes 140, 240 of the devices and the spacer 503 positioned to slide in the gap that exists between the top member 110, 210 and bottom member 120, 220 when these two elements are operatively positioned.

Figure 28:
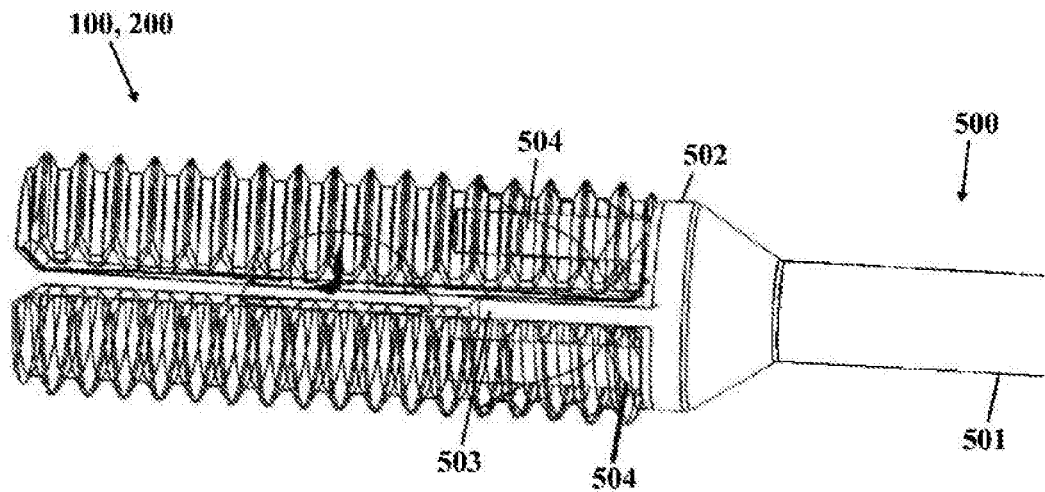
FIG. 28 is an enlarged perspective elevational view of the insertion tool of FIG. 26 inserted into the disc replacement device of FIG. 1, in accordance with an aspect of the present invention.
Figure 29:
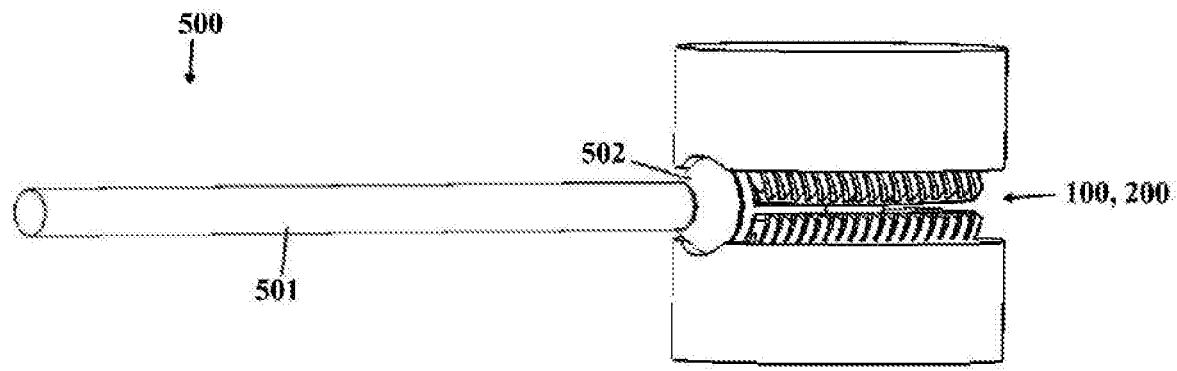
FIG. 29 is a perspective elevational view of the insertion tool of FIG. 26 inserted into the disc replacement device of FIG. 1 following implantation of the disc replacement device between two vertebral bodies, in accordance with an aspect of the present invention.
Figure 30:
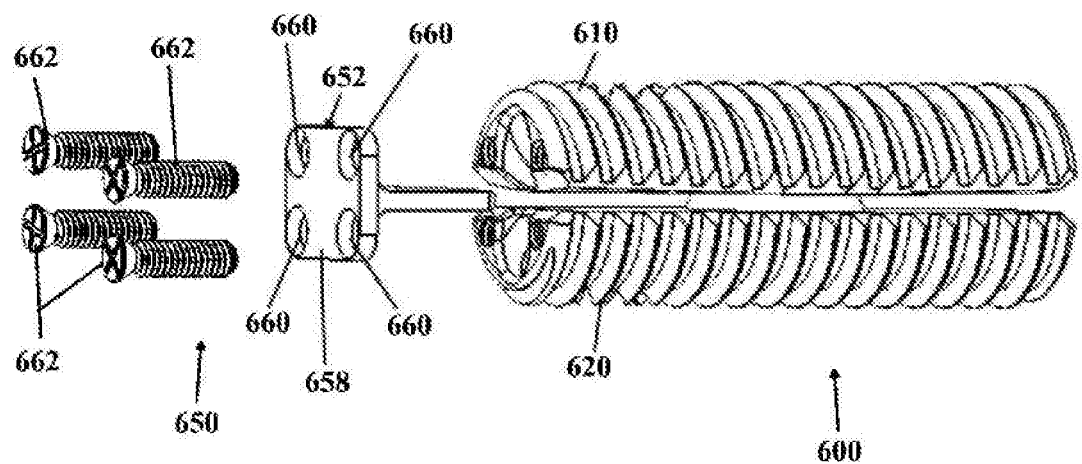
FIG. 30 is a partially exploded perspective view of an alternative embodiment of a disc replacement device, showing a top member, a bottom member and a means to restrict motion, in accordance with an aspect of the present invention.
Figure 31:
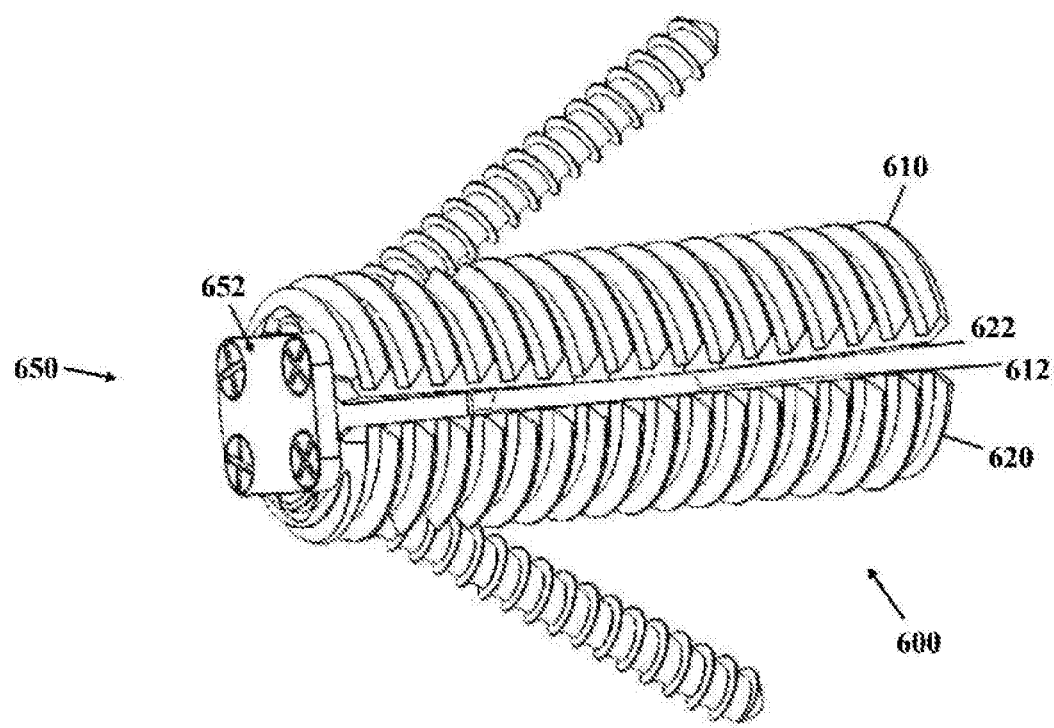
FIG. 31 is a perspective view of the assembled alternative embodiment of a disc replacement device seen in FIG. 30 with the fixation screws in position, in accordance with an aspect of the present invention.
Figure 32:
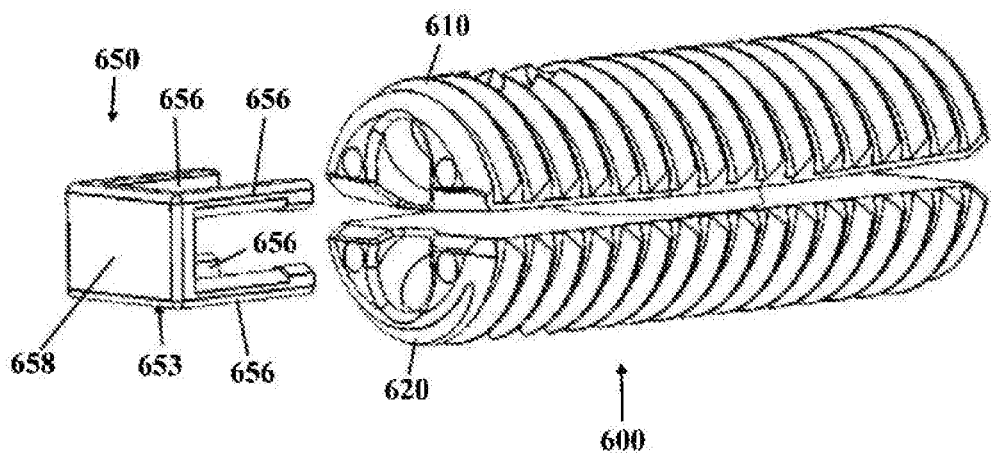
FIG. 32 is a partially exploded perspective view of an alternative embodiment of a disc replacement device, showing a top member, a bottom member and an alternative embodiment for a means to restrict motion, in accordance with an aspect of the present invention.
Figure 33:
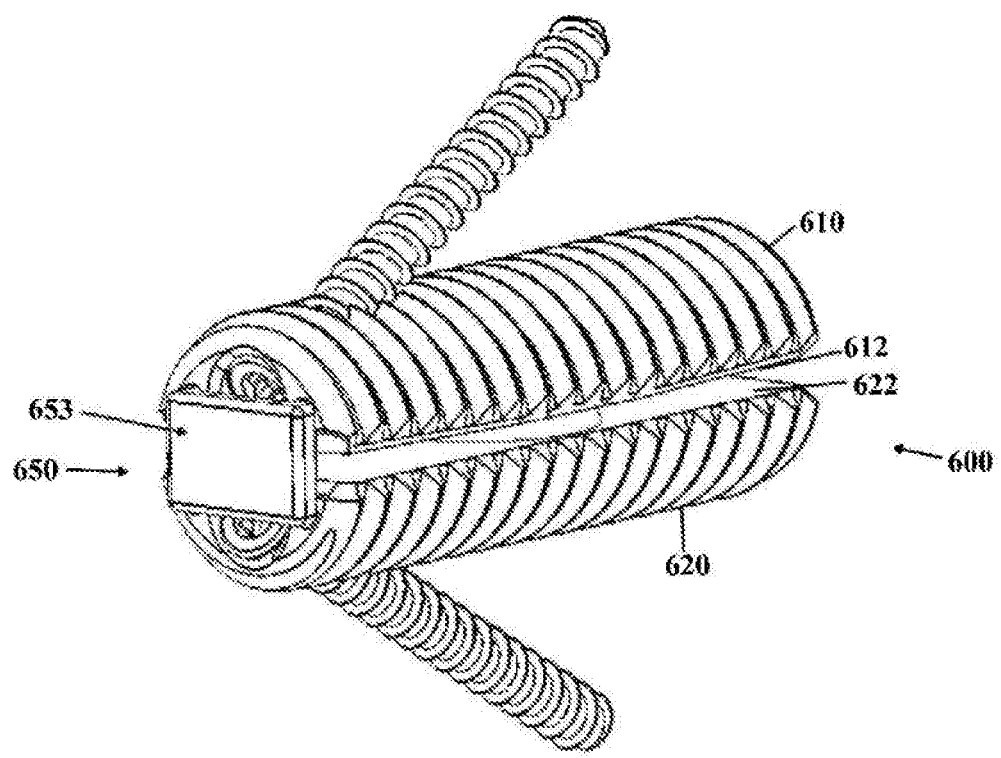
FIG. 33 is a perspective view of the assembled alternative embodiment of a disc replacement device seen in FIG. 32 with the fixation screws in position, in accordance with an aspect of the present invention.

FIG. 28 further shows the instrument 500 following engagement with the device 100, 200. The prongs 504 extend into the holes 140, 240 while the spacer 503 slides into the slot that exists between the two assembled members. The head 502 is juxtaposed to the front portions to the top and bottom members, 110, 210 and 120, 220 respectively. As seen in FIG. 29, the instrument is used to insert the device 100, 200 into the space that exists between two adjacent vertebral bodies. The instrument 500 is multi-functional in that it holds the assembled device 100, 200 together for threading the device into the bone. The instrument 500 may also be used to actually thread the device 100, 200 into the bone. Further, although not shown, the instrument 500 may function as a drill guide for drilling the pilot holes into which the bone fixation devices 130, 230 are inserted.

The example surgical method for using either of the embodiments of the disc replacement devices 100, 200 is well known in the art, including the appropriate lateral surgical exposure and dissection techniques. However, the devices 100, 200 may be inserted using two distinctly different surgical procedures, one using an open exposure, or alternatively, using minimally invasive techniques. In the open technique, a long oblique incision is made on the patients flank and general abdominal retractors are used to expose the abdominal musculature. The muscles are opened and similarly retracted. After dissecting the retroperitoneal space the iliopsoas muscle is retracted and the disc space is exposed. The disc space is then drilled, tapped and the device 100, 200 is inserted and held in place with the locking screws 230 through the insertion holes 240. In the minimally invasive technique the procedure is modified to be performed through a 3 cm incision. All muscle and soft tissue is retracted via tubular retractors inserted over a series of dilators based a guide wire inserted into the disc space. Thereafter, the same procedure is performed, but through the minimal access tubular retractor.

The method includes, obtaining the properly sized and configured device 100, 200 relative to the target vertebral end plates that will be opposing the external surfaces of the top member and the bottom member. A pilot hole is drilled that transects the interbody space following the resection of the diseased/damaged disc. An insertion tool 500 is used to engage and secure the assembled device 100, 200. The insertion tool 500 is positioned adjacent the pilot hole with the assembled device 100, 200 locked to the proximal end. The insertion instrument 500 with the assembled device 100, 200 is rotated, screwing the device 100, 200 into the pilot hole until the device 100, 200 is appropriately positioned within the vertebral end plates of the adjacent vertebral bodies. Imagining technology is used to confirm proper spacing and positioning has been achieved. Once this is confirmed, the insertion tool is disengaged and removed from the body.

The additional steps of drilling the holes and inserting the bone fixation devices 130, 230 may also be completed once the device 100, 200 is in its final position.

Figure 22:
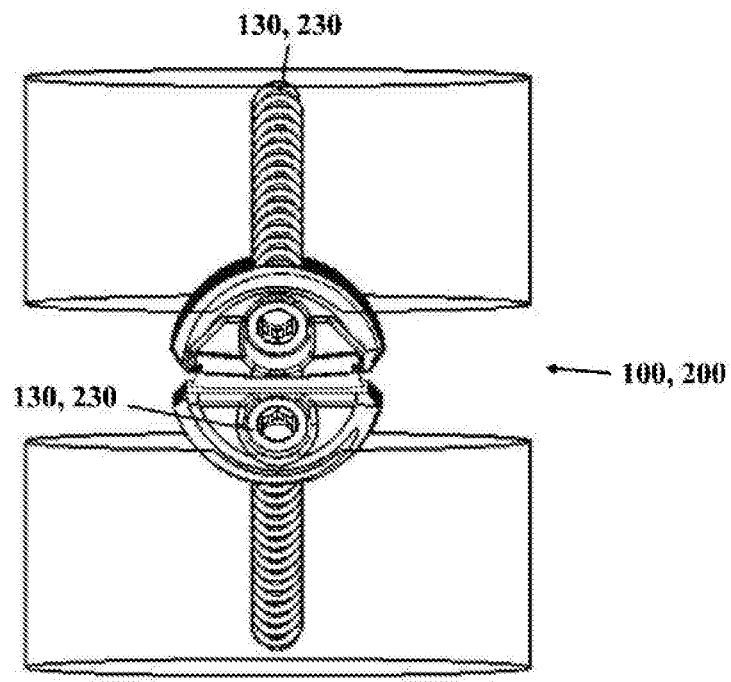
FIG. 22 is front elevational view of the disc replacement device of FIG. 13, implanted between two vertebral bodies, in accordance with an aspect of the present invention.
Figure 23:
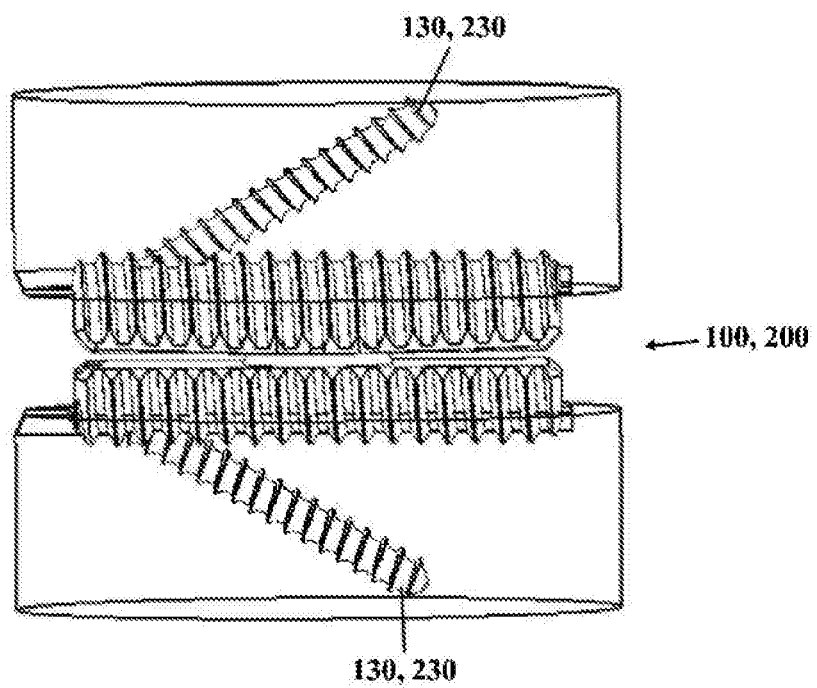
FIG. 23 is side elevational view of the disc replacement device of FIG. 13, implanted between two vertebral bodies, in accordance with an aspect of the present invention.
Figure 24:
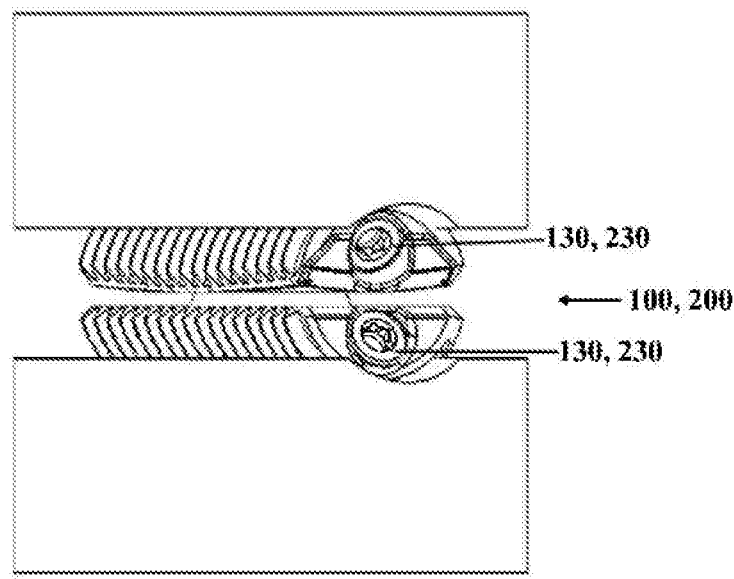
FIG. 24 is perspective elevational view of the disc replacement device of FIG. 13, implanted between two vertebral bodies, in accordance with an aspect of the present invention.
Figure 25:
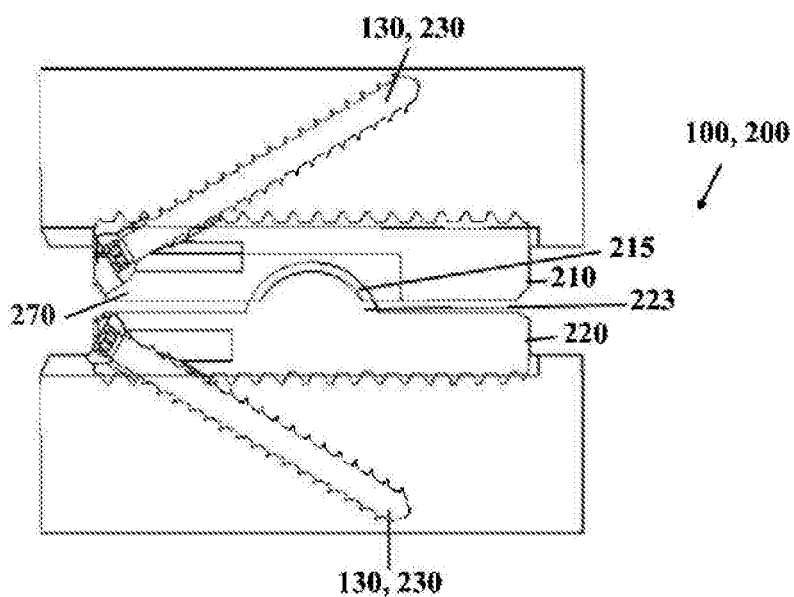
FIG. 25 is sectional view of the side elevational view of FIG. 23 showing the disc replacement device of FIG. 13, implanted between two vertebral bodies, in accordance with an aspect of the present invention.
Figure 26:
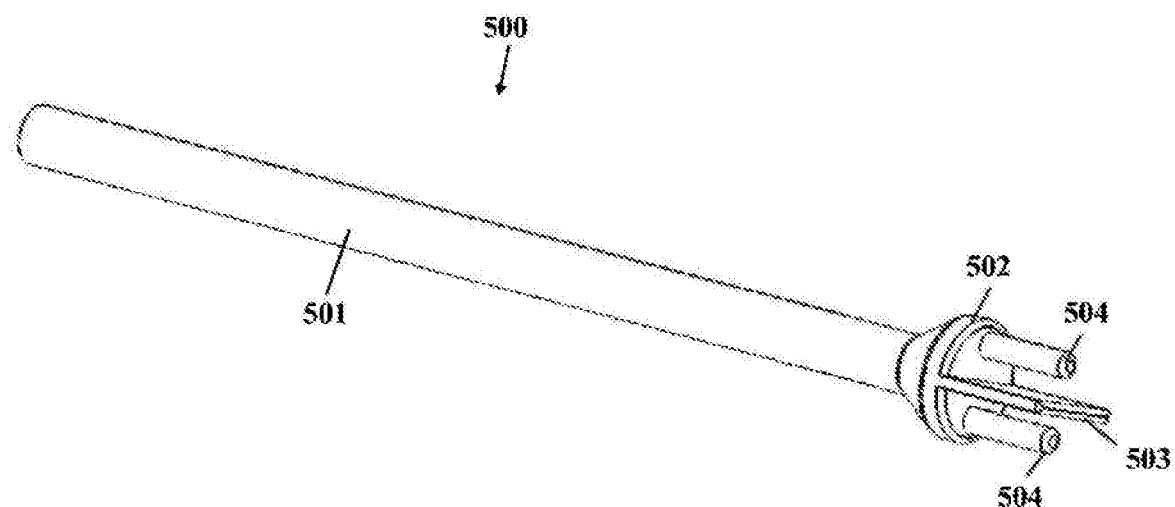
FIG. 26 is perspective elevational view of an insertion tool for a disc replacement device, in accordance with an aspect of the present invention.

FIGS. 22-24 show various views of the device 100, 200 in between two vertebral bodies with the bone fixation devices 130, 230 secured through the device and into the adjacent bone. A side sectional view of the implanted device 100, 200, including the bone fixation devices 230 is seen in FIG. 25. The sectional view shows how the ball 223 and the bearing insert 270, specifically the socket 215 are aligned. The bone fixation devices 230 are also shown as locking the bearing insert 270 in position so as to ensure no movement of the bearing insert 270 when articulation occurs between the top and bottom members 210, 220.

Figure 34:
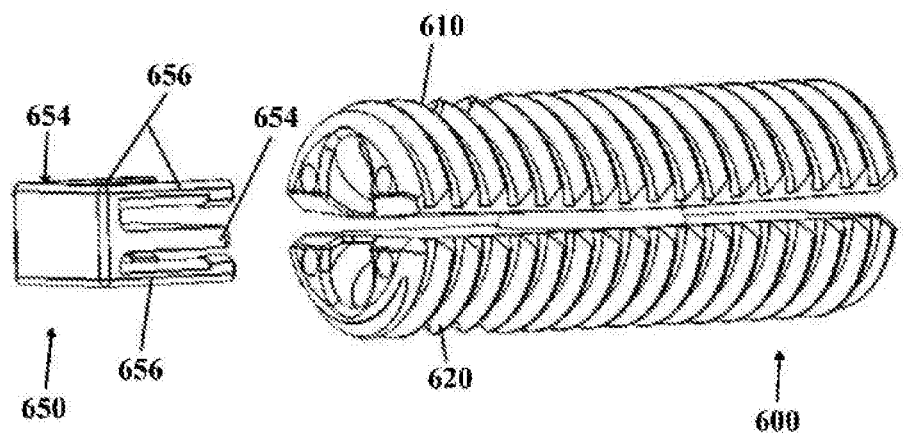
FIG. 34 is a partially exploded perspective view of an alternative embodiment of a disc replacement device, showing a top member, a bottom member and an alternative embodiment for a means to restrict motion, in accordance with an aspect of the present invention.
Figure 35:
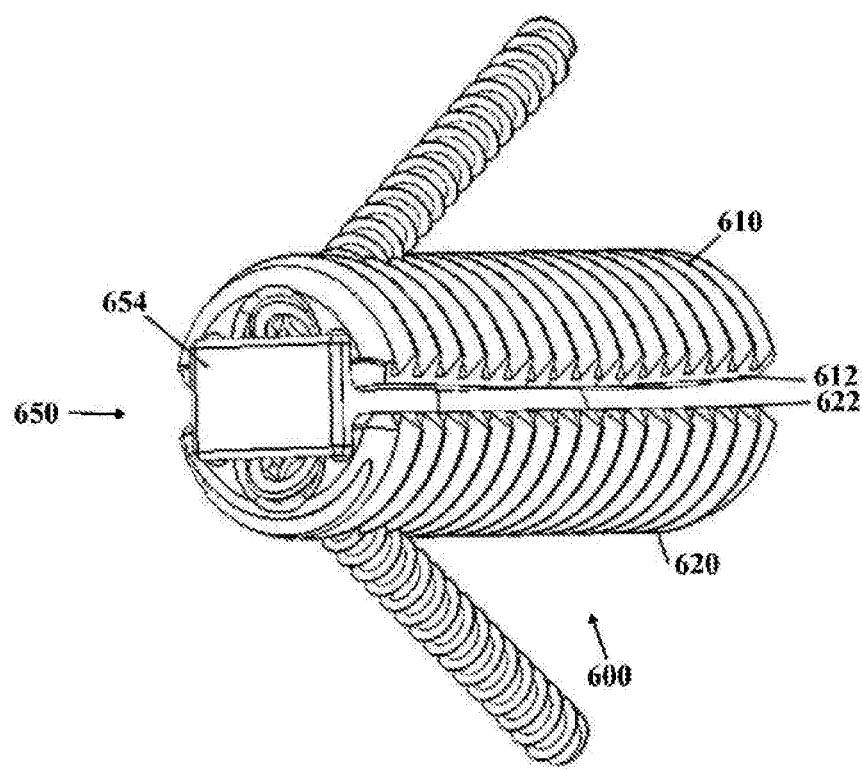
FIG. 35 is a perspective view of the assembled alternative embodiment of a disc replacement device seen in FIG. 34 with the fixation screws in position, in accordance with an aspect of the present invention.
Figure 36:
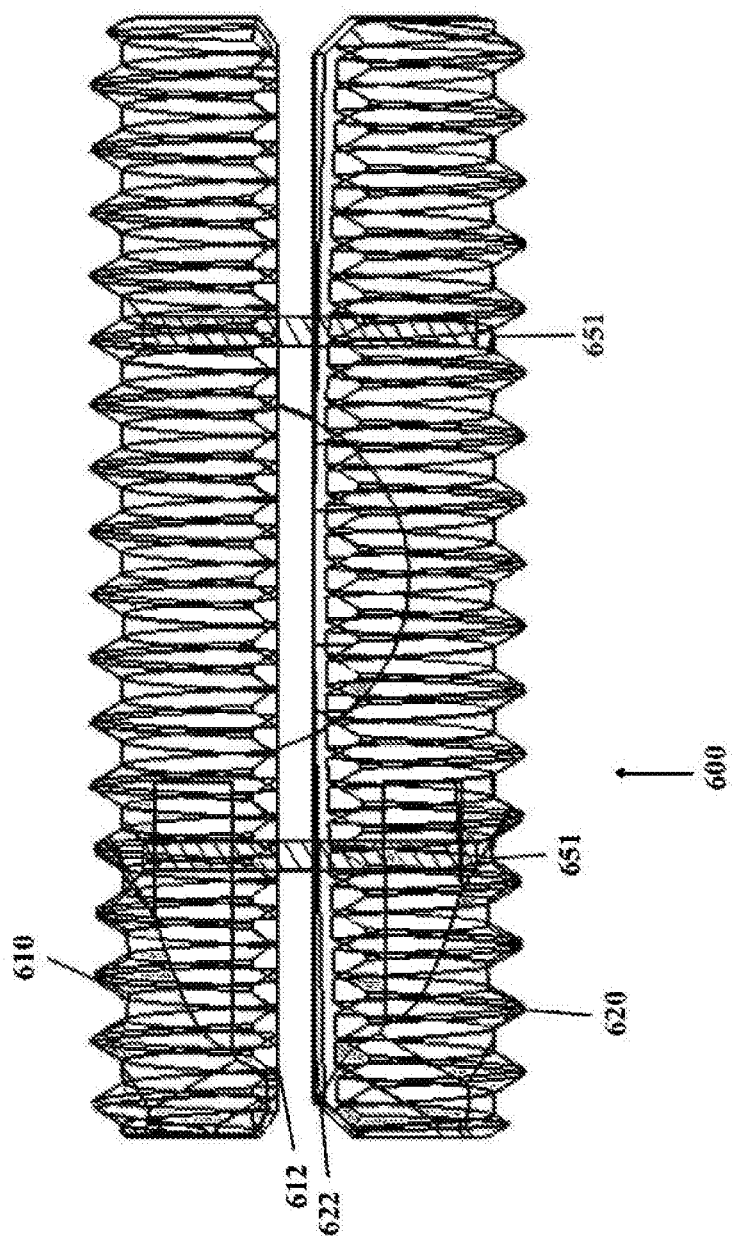
FIG. 36 is an elevational view of an alternative embodiment of a disc replacement device, showing a top member, a bottom member and an alternative embodiment for a means to restrict motion that includes a plurality of superior to inferior extending screws, in accordance with an aspect of the present invention.

Further embodiments of a disc replacement device are seen in FIGS. 30-36. Specifically, as seen in the exploded views shown in FIGS. 31, 33 and 35 and also an elevated view as shown in FIG. 36, a means to restrict motion 650 between the top and bottom members 610, 620 is included to convert the disc replacement device from a motion device 100, 200 to a fusion device 600. The same structural elements as described above for device 100 are seen in device 600, but for brevity sake, these will not be described again in detail here as such elements will include the same characteristics and functionality as disclosed above.

FIG. 36 shows for example, the means to restrict motion as a plurality of screws 651 that are inserted through the top member 610 into the bottom member 620 on each side of the articulating surfaces 612, 622, thereby fixating the two members together and inhibiting motion therebetween. After the device 600 has been fixed, it can be threaded into the upper and lower vertebral bodies creating a space into which fusion material can be packed to facilitate stabilization and fusion between the vertebral bodies.

Alternatively, as seen in FIGS. 30-35, the means to restrict motion may also include a locking device, such as a "T-pin" or T-shaped member 652 (with screws) (see FIGS. 30 and 31), a "U-pin" or U-shaped member 653 (see FIGS. 32 and 33) or a "U-pin" or U-shaped member with middle spacer 654 (see FIGS. 34 and 35). The means to restrict motion 650 for the embodiments seen in FIGS. 30-35 may be inserted into the ends of the top member 610 and bottom member 620 on both sides and lateral to the articulating surfaces 612, 622. These three examples of types of means to restrict motion provides the surgeon with the option to change the device 600 from a dynamic device into a static or fusion device post-insertion between the vertebral bodies. For these embodiments the means to restrict motion is inserted into the ends of the top member 610 and bottom member 620 on both sides and lateral to the articulating surfaces 612, 622. A portion (pins, posts, screws, deployable fins, ribbed cylinders, tapered posts, etc.) of the means to restrict motion or at least one protrusion is (are) inserted to a depth into the top and bottom members 610, 620 to immobilize the two members relative to each other. The at least one protrusion 654, 656 extends perpendicular from a plate 658 which mates with the front aspects of the top member 610 and bottom member 620. The at least one protrusion 654 may be a center protrusion of insertion into the opening between the top and bottom members 610, 620. Alternatively, the at least one protrusion 656 may be legs around the perimeter of the plate 658, in the depicted embodiment there are four protrusions 656 at the corners of the plate 658. In yet another embodiment, the at least one protrusion 656 may include both a center protrusion and at least one leg positioned on the perimeter of the plate 658. The plate 658 may include openings 660 for inserting at least one fastener 662 into the top member 610 and bottom member 620 to fix the members 610, 620 together. In the depicted embodiment of FIGS. 30 and 31, there are four openings 660 and four fasteners 662. Once fixed, the implanted device 600 may, optionally, be rotated 90 degrees from its original insertion position. The space between the top member 610 and bottom member 620 is positioned to create a channel or span between the upper and lower vertebral bodies that will accommodate fusion material and enable bone fusion to occur across the distance between the two vertebral bodies.

Although the example embodiments have been depicted and described in detail herein, it will be apparent to those skilled in the relevant art that various modifications, additions and substitutions can be made without departing from its essence and therefore these are to be considered to be within the scope of the following claims.

What is claimed is:

1. A surgical method for maintaining a space between two vertebral bodies in a spine of a patient, comprising:
   obtaining a medical device comprising:
      a bottom body member having an outer surface, an inner surface, and a first opening extending through the bottom body member to the outer surface, wherein a portion of the inner surface is convex;
      a top body member having an outer surface, an inner surface, and a second opening extending through the top body member to the outer surface, wherein the inner surface defines a channel; and
      a bearing insert member having a flat top surface and a bottom surface comprising a concave portion;
   assembling the medical device by sliding the bearing insert member within the channel to operatively connect the bearing insert member to the channel of the top body member, and positioning the bearing insert member relative to the bottom body member such that the concave portion of the bearing insert member articulates with the convex portion of the bottom body member;
   obtaining a holding tool having a handle and a head extending away from a first end of the handle, wherein the head includes a spacer and at least one prong;
   inserting the spacer into a gap within the medical device and the at least one prong into at least one of the first opening and the second opening to couple the holding tool within the medical device;
   inserting the medical device into the space between the two vertebral bodies; and
   disengaging the holding tool to remove the holding tool from an opening in the patient.

2. The surgical method of claim 1, further comprising:
   drilling a first hole through the first opening in the bottom body member into a first vertebra and drilling a second hole through the second opening in the bearing insert member and the top body member into a second vertebra; and
   inserting a first bone fixation device through the first opening and a second bone fixation device through the second opening.

3. The surgical method of claim 2, wherein inserting further comprises rotatably implanting the medical device into the space between the two vertebral bodies using a surgical procedure selected from an open exposure procedure and a minimally invasive technique.

4. The surgical method of claim 3, further comprising:
   inserting the first bone fixation device into the first opening and the second bone fixation device into the second opening; and
   securing the medical device to the two vertebral bodies.

5. The surgical method of claim 2, wherein the top body member includes a front surface and a rear surface, the bearing insert member includes a front surface, and the bottom body member includes a front surface and a rear surface.

6. The surgical method of claim 5, wherein the first opening in the bottom body member extends from the front surface of the bottom body member to the outer surface of the bottom body member; and
   the second opening in the top body member extends from the front surface of the top body member to the outer surface of the top body member.

7. The surgical method of claim 6, wherein the first opening and the second opening are each angled, wherein the angles range from about 10 degrees to about 45 degrees.

8. The surgical method of claim 5, wherein the front surfaces of the top body member, the bearing insert member, and the bottom body member include a front relief edge and the rear surfaces of the top body member and the bottom body member include a rear relief edge.

9. The surgical method of claim 2, wherein the two bone fixation devices are selected from bone screws, posts, deployable fins, nails, pegs, and pins.

10. The surgical method of claim 1, wherein the concave portion of the bearing insert member is configured as at least one of a sphere and a ball to permit at least one of translation and rotation of the convex portion of the bottom body member.

11. The surgical method of claim 1, wherein the outer surfaces of the top body member and the bottom body member are generally arcuate.

12. The surgical method of claim 11, wherein disposed on the outer surfaces of the top body member and bottom body member are at least one of threads, ribs, spikes, scallops, and porous coating.

13. The surgical method of claim 11, wherein the outer surface of the top body member and the bottom body member are coated with a bone growth sub stance.

14. The surgical method of claim 1, further comprising:
a locking device including a plate and at least one leg extending perpendicular from the plate.

15. The surgical method of claim 14, wherein the at least one leg is disposed between the top body member and the bottom body member and the plate of the locking device pressingly contacts the front surfaces of the top body member, the bearing insert member and the bottom body member.

16. The surgical method of claim 14, wherein the locking plate further comprises at least two openings.

17. The surgical method of claim 16, wherein the locking device further includes at least two fastening mechanisms for insertion through the at least two openings and extending through the plate and into at least two of the top body member, the bearing insert member, and the bottom body member to couple the top body member, the bearing insert member, and the bottom body member together.

18. The surgical method of claim 1, wherein the top body member and the bottom body member are comprised of a biocompatible material, selected from the group comprising: PEEK, titanium, cobalt chromium and stainless steel.

19. The surgical method of claim 1, wherein the bearing insert member is modular.

* * * * *